United States Patent [19]

Chaney

[11] Patent Number: 5,313,271
[45] Date of Patent: May 17, 1994

[54] ABSOLUTE GAS REFRACTOMETER WHEREIN THE OPTICAL PATH DIFFERENCE OF SAID REFRACTOMETER IS FIXED

[75] Inventor: Raymond J. Chaney, Berkeley, United Kingdom

[73] Assignee: Renishaw Transducer Systems Limited, Gloucestershire, United Kingdom

[21] Appl. No.: 845,711

[22] Filed: Mar. 4, 1992

[30] Foreign Application Priority Data

Mar. 8, 1991 [GB] United Kingdom ................ 9104897
Aug. 20, 1991 [GB] United Kingdom ................ 9117921

[51] Int. Cl.$^5$ ............................................. G01B 9/02
[52] U.S. Cl. ......................................... 356/361; 356/358
[58] Field of Search .................. 356/345, 361, 358, 128

[56] References Cited

U.S. PATENT DOCUMENTS

| | | |
|---|---|---|
| 4,215,938 | 8/1980 | Farrand et al. |
| 4,733,967 | 3/1988 | Sommargren |
| 4,765,741 | 8/1988 | Detro et al. |
| 4,813,783 | 3/1989 | Torge ................................ 356/358 |

FOREIGN PATENT DOCUMENTS 0094836  11/1983  European Pat. Off.

Primary Examiner—Samuel A. Turner
Assistant Examiner—Robert Kim
Attorney, Agent, or Firm—Oliff & Berridge

[57] ABSTRACT

A gas refractometer is disclosed for use with a measurement interferometer and which in its simplest form (FIG. 1) comprises an auxiliary interferometer which uses the same light source as the measurement interferometer and which provides two light paths therethrough of different lengths. The gas refractometer operates as a tracking interferometer by providing a signal indicative of changes in the refractive index of the atmosphere in which the measurement interferometer is operating. At the same time the gas refractometer is made to act as an absolute refractometer by arranging that the maximum change in the difference between the two path lengths within the refractometer which will be produced for the full range of refractive index variation under which measurements are likely to be made will be less than one wavelength of the light used. Various embodiments of the refractometer are described including variants in which two auxiliary interferometers are used, and the use of the refractometer output to correct the measurement interferometer reading or to control the wavelength of the light used is also described.

18 Claims, 4 Drawing Sheets

ABSOLUTE GAS REFRACTOMETER WHEREIN THE OPTICAL PATH DIFFERENCE OF SAID REFRACTOMETER IS FIXED

The present invention relates to absolute gas refractometers.

In a measuring operation, for example, measuring a distance using a laser interferometer, the output of the detector system provides a fringe count which is a measurement of the distance in terms of a number of wavelengths of light.

The wavelength of light however, varies with any variation in the frequency of the light source, and with atmospheric conditions.

In the past the problem of frequency variation has been dealt with by providing a closed loop control system on the laser to stabilise its frequency. The problem of the variation of wavelength with atmospheric conditions has been solved by the provision of a tracking air refractometer to directly measure the refractive index of the air during the measuring operation. The measurements obtained are then used to compensate the measurements being made by the measuring interferometer for any variations in the refractive index. An example of such a tracking interferometer is described in U.S. Pat. No. 4,215,938. Such a system however, does not give a measurement of the absolute value of the refractive index of the air, and this value still has to be obtained from an absolute air refractometer, or from a so-called weather station which measures the local temperature pressure and humidity of the atmosphere, from which the refractive index of the air can be calculated.

The additional requirement for an absolute measure of the refractive index adds costs to the measuring system.

The present invention provides an air refractometer for an interferometric measuring apparatus which provides not only a continuous measurement of any changes in the refractive index of air during a measuring operation, but also provides measurement of the absolute value of the refractive index of the air.

In accordance with the present invention, there is provided a gas refractometer comprising a light source for generating a light beam, beam splitting means which is positioned to receive at least a portion of said light beam at least one reflector disposed in relatively fixed relationship with the beam splitting means to define first and second optical paths of different lengths for said light beam through the refractometer and detector means for producing an output signal indicative of a change in the difference between the two optical path lengths caused by changes in the refractive index of the gas, characterised in that the beam splitting means and the reflector are so designed and arranged that the maximum change in the difference between the two optical path lengths within the refractometer which will be produced for the full range of refractive index variation under which measurements are likely to be made will be less than one wavelength of the light used.

The refractometer operates as an interferometer having two different fixed physical path lengths therethrough, but in which the optical path lengths vary if the refractive index of the atmosphere within the refractometer changes. The change in the differential path length produces a fringe count difference in the detector as the refractive index varies. The refractometer thus acts as a tracking interferometer. However, because of the limitation on the differential path length imposed by the present design, and because the range of the absolute refractive index of the atmosphere in which it will operate is known the refractometer will also act as an absolute refractometer.

For a refractometer operating in air using a Helium-Neon laser for the light source, the differential path length through the refractometer may be of the order of 6 mm to avoid the fringe count exceeding one whole fringe while the refractive index of air changes over a range of 100 parts per million (ppm).

Thus, if the refractometer is initially calibrated against air at standard temperature, pressure and humidity, and the atmospheric conditions when the refractometer is switched on have not varied from the standard conditions sufficiently to have caused a change in refractive index of more than ±50 ppm, then the reading of the refractometer will give the absolute change in refractive index from standard conditions.

It is to be understood that the interferometer need not necessarily be calibrated against standard conditions but any suitable known conditions can be used, and that the differential path length may be set to provide for absolute measurement of refractive index over a greater or smaller range than 100 ppm.

It is also to be understood that the refractometer of the present invention may be used with other types of laser, e.g. a diode laser, and in other atmospheres in which case the refractometer may be constructed to have a path length differential other than 6 mm for a 100 ppm range.

Two significant uses may be made of the signal from the detector of the refractometer of the present invention. First it may be used as a post-processing signal to correct the measurements of a measuring interferometer. For this purpose the refractometer is used as an auxiliary interferometer using part of the beam from the light source of the measuring interferometer and open to the same atmospheric conditions.

Second it may be used as a pre-processing signal to change the frequency of the light source with which it is used to keep the wavelength of the light beam at a constant value. Specifically, a laser diode which has a relatively large tunable frequency range, can be pre-processed with the refractometer of the present invention. This enables a diode laser to be used in a length measuring interferometer without the need for post-processing the measurements made thereby.

Various designs may be used for the air refractometer. For example, a standard Michelson or Mach Zehnder interferometer, or even a symmetrical plane mirror or glass block arrangement which provides two different path lengths for a light beam from an inlet to an outlet thereof, and in which the beam undergoes the same number of reflections and transmissions.

Two important design criteria to be observed in preferred embodiments of the invention are that the beam passing through the refractometer and split into two different path lengths should meet the same number of surfaces and pass through the same thickness of material in both of the path lengths.

In preferred embodiments of the invention, the refractometer is constructed as two interferometers each having a differential path length therein, but where the detector signal is generated from a path length which is the difference between the two interferometer path length differentials.

The invention will now be more particularly described, by way of example only, with reference to the accompanying drawings in which.

Figure 1:
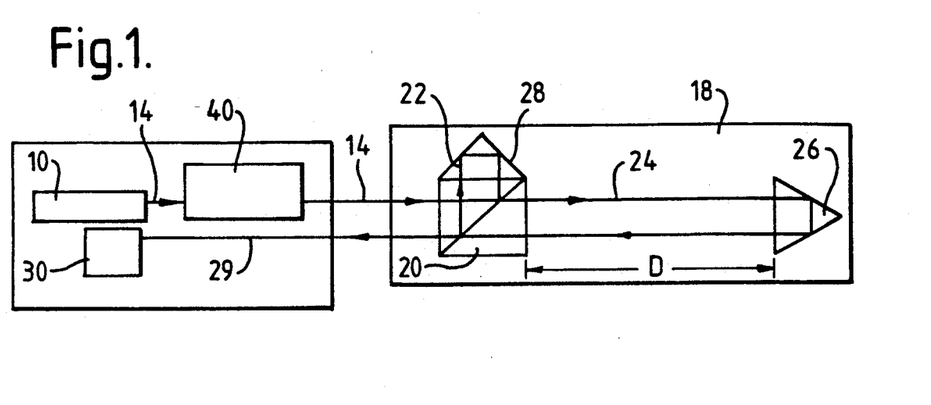
FIG. 1 is a diagrammatic layout of an interferometric measuring apparatus including a refractometer of the present invention.

Referring now to the drawings, there is shown in FIG. 1 a distance measuring interferometer of the Michelson type indicated generally by reference numeral 18, and which includes a laser light source 10, which generates a light beam 14 of nominal wavelength $\lambda(\text{air})$ in air of refractive index n.

The Michelson interferometer includes a beam splitter 20 which receives the beam 14, and generates therefrom a reference beam 22 and a measuring beam 24. In this example the beam splitter 20 remains static and the measuring beam 24 is directed towards a movable retro-reflector 26, while the reference beam 22 is directed towards a retro-reflector 28 which is mounted in fixed relation with the beam splitter 20.

The beams returning from the retro-reflectors 26 and 28 are re-combined in the beam splitter, and the combined beam 29 is passed to a detector 30 which, in known manner produces a fringe count which is representative of the change in the distance D between the movable retro-reflector and the beam splitter. It is to be understood that in a measuring operation, the fixed and movable retro-reflectors are mounted on two relatively movable parts of an apparatus the relative movements of which are to be measured.

The distance D is calculated from the product $m\lambda(\text{air})$, where m is the fringe count generated by the detector system. The wavelength $\lambda(\text{air})$ is however variable due both to the variation in the refractive index of air with the temperature, pressure and humidity of the air, and also to any variation in the frequency of the beam generated by the laser. In order to provide a real-time correction factor for the wavelength variation, which can, inter alia be applied to correct the measurement values provided by the measuring interferometer, an air refractometer in the form of an auxiliary interferometer 40 is mounted in close relation to the laser and open to the atmosphere. In the present example the auxiliary interferometer is a Mach Zehnder interferometer which is shown in greater detail in FIG. 2.

Figure 2:
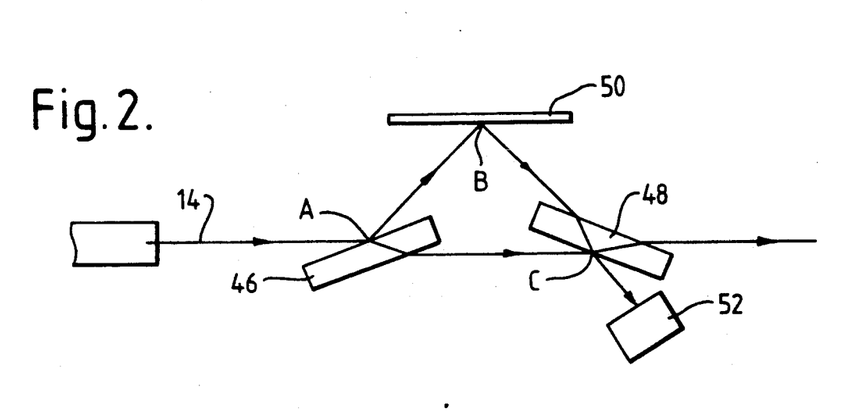
FIG. 2 is a detailed view of an auxiliary interferometer used as a refractometer in the apparatus of FIG. 1.

The Mach Zehnder interferometer consists of two angled glass blocks 46, 48 and a plane mirror 50. The incoming light beam 14 meets the top surface of glass block 46 at point A and is partially reflected towards the mirror 50 and partially transmitted to the glass block 48. The reflected part of the beam strikes the mirror 50 at point B and is reflected towards the glass block 48. At the glass block 48 the reflected part of the beam and the transmitted part are re-combined at point C, and the combined beam is passed to a detector 52 which is capable of detecting interference fringes in the combined beam.

The Mach Zehnder interferometer is designed so that the path length ABC of the reflected part of the beam and the path length AC of the transmitted part of the beam are different, so that any change in the refractive index of air, or any change in the frequency of the laser beam, will result in a detectable change in the fringe pattern observed by the detector 52.

Assuming for the moment that there is no variation in the path lengths ABC and AC due to thermal expansions of the parts of the auxiliary interferometer, or to pressure variations, the physical path difference $L = ABC - AC$ will be constant. The optical path length, however, will vary with the refractive index (n) of air, so that the fringe count given by the interferometer 40 will vary if the refractive index of the air varies, and this provides a direct indication of the refractive index changes.

The auxiliary interferometer thus acts as a tracking air refractometer. A preferred feature of the present invention however, is that by careful selection of the parameters of the auxiliary interferometer, it can be designed effectively to act as an absolute air refractometer. The theory behind this is as follows. The refractive index in air is known to be 1.000292 at standard ambient conditions. If therefore, the auxiliary interferometer is designed so that it will register a change in fringe count of less than one in recording the greatest change in the refractive index of air from this value which is likely to be encountered in making measurements in most countries throughout the world, then the change in fringe count recorded effectively provides an absolute value of refractive index, by adding or subtracting the calibrated change in refractive index to the value 1.000292. Thus it is desirable for many measurement applications that the auxiliary interferometer detector has the capability of interpolating down to very small fractions (e.g. less than one hundredth) of a fringe count, but this is well within the resolution of present day interpolators.

The criteria for the design of the auxiliary interferometer are as follows:

a) Select the maximum range of variation of refractive index $\Delta n$ which it is required to tolerate. This could, for example, be $\Delta n = 100$ ppm (parts per million).

b) Select the wavelength in air, $\lambda(\text{air})$, of the light to be used. For example, using a Helium-Neon laser this could be 0.6 microns.

c) Calculate the physical path length difference L required such that the optical path length variation caused by a change in the refractive index of air $\Delta n$ of 100 ppm will not give rise to an interferometer fringe count variation $\Delta m$ of one complete fringe as follows:

Since one fringe count $m =$ one wavelength change, $\lambda(\text{air})$

| | |
|---|---|
| max $\Delta m = \lambda$ air $= 0.6$ microns $= 0.6 \times 10^{-6}$ | 1 |
| max $\Delta n = 100$ ppm $= 100 \times 10^{-6}$ | 2 |
| The optical path length is nL, and since L is assumed to be | 3 |

-continued fixed, any change in optical path length can be written as L. Δn

To fulfil the above criterion L. Δn must be less than λ(air) thus L must be less than λ(air)/Δn                    4

By substituting from equations 1 and 2, L = 6 mm.

Having made the interferometer such that ABC-AC is 6 mm or less it needs to be calibrated to determine what L actually is.

A possible calibration procedure is to place the interferometer in a sealed environment and pump it down to vacuum pressure. With the interferometer operating using light of a known, constant wavelength in vacuum $\lambda_v$ from an accurately frequency stabilised laser, air is then allowed into the sealed environment at known conditions of temperature, pressure and humidity which are close to the centre of the working range of conditions of the distance measuring interferometer. The change in the interferometer fringe count Δm is recorded.

The known conditions of the air allow its refractive index n to be determined. The change in refractive index from vacuum to the known value of the air thus gives the value of Δn. In this instance the value of Δn is actually equal to n because the refractive index of vacuum is unity.

Alternatively the auxiliary interferometer may be calibrated against an accurate air refractometer.

The wavelength of the light in air, λ(air), can be calculated if required from the relationship $\lambda(air) = n\lambda_v$.

Having obtained the values of $\lambda_v$, n, and Δm they are used to provide a correction factor for the distance measuring interferometer as follows:

Within the Mach Zehnder interferometer the distance ABC can be written in terms of the product of a fringe count m and the wavelength of light λ used, so that at the calibration set up in vacuum distance $ABC = m_1 \lambda_v$
and,
distance $AC = m_2 \lambda_v$
hence
$ABC - AC = L = (m_1 - m_2), \lambda_v$ For measurements in air the value of λ will change to λ(air) but since $\lambda(air) = n.\lambda_v$ we can write as a general equation $$L = (m_1 - m_2) \cdot n \lambda_v \quad 5$$

At the calibration set up with the interferometer in vacuum, neither $(m_1 - m_2)$ nor L are known. However n=1 for a vacuum, and the value of $\lambda_v$ is constant and known. The reading on the interferometer can be set at O and as the air is allowed in, the interferometer reading changes because the optical path lengths ABC and AC change as the refractive index increases from n=1 to $n = n_1$.

We can thus write for the air of known refractive index $n_1$.

distance $ABC = m'_1 \cdot n_1 \cdot \lambda_v$
and
distance $AC = m'_2 \cdot n_1 \cdot \lambda_v$
so that
$L = (m'_1 - m'_2) \cdot n_1 \cdot \lambda_v$ Since we assume that the physical length L has not changed we can write $(m_1 - m_2) \cdot \lambda_v = (m'_1 - m'_2) \cdot N_1 \cdot \lambda_v$ Since for the calibration process $\lambda_v$ is constant we have $$m_1 - m_2 = (m'_1 - m'_2) \cdot n_1$$

the fringe count gives the value of $(m'_1 - m'_2) = \Delta_m'$ which is a number, and since $n_1$ is also a known number we can write the product $\Delta_m' \cdot n_1$ as a constant K giving $m_1 - m_2 = K$ \quad 6 and $L = K\lambda_v = K_1$ \quad 7

Any future readings from the Mach Zehnder interferometer will be made in air with refractive index $n_2$ at or near the same value of $n_1$ (i.e. within the ±50 ppm range for which the interferometer has been designed without registering a whole fringe count change).

Any further readings taken from the Mach Zehnder interferometer at different conditions will provide a new fringe count $\Delta_m'' = m_1'' - m_2''$.

Once again $L = \Delta_m'' \cdot \lambda_v'' \cdot n_2$ where $n_2$ is the new unknown refractive index of air and $\lambda_v''$ is a new value for the wavelength of the laser light in vacuum, (which with a frequency stabilised laser would be equal to $\lambda_v$). substituting for L from equation 7

$$\frac{K_1}{\Delta_m''} = \lambda_v'' \cdot n_2$$

Unless the frequency of the laser is very accurately controlled $\lambda_v''$ may not be equal to $\lambda_v$ and will contribute an error in the distance interferometer reading along with any error introduced by the change of refractive index.

However, the distance D, measured by the distance measuring interferometer, can also be written in terms of a fringe count m times the wavelength of the laser light in air, λ(air) or $m.n.\lambda_v$.

Since the Mach Zehnder interferometer and the distance measuring interferometer both use the same laser beam, and are exposed to the same atmosphere the value of the product $n.\lambda_v$ is the same for both and the Mach Zehnder interferometer can provide this product.

Since the distance measuring apparatus cannot differentiate between a change in wavelength of the light due to a frequency change and that due to a change in refractive index, the value of the product $n\lambda_v$ is an ideal correction factor to apply to the distance measurement since it takes account of both.

The error range selected for the refractive index change which the Mach Zehnder interferometer could deal with was ±50 ppm. Provided the error due to varying frequency of the laser is small i.e. up to say 5 ppm there is no danger of the total error being such as to cause a whole fringe count change in the Mach Zehnder interferometer reading. Present laser stabilisation techniques have grown more sophisticated and expensive in an attempt to stabilise frequencies to one tenth or even one hundredth of a part per million. By including the auxiliary interferometer which corrects for ±50 ppm, and allowing say 5 ppm of this error budget to be accounted for by frequency changes, it is no longer necessary to correct the laser frequency to such a degree of accuracy. Thus simpler, less costly, stabilisation techniques can be used to keep the laser wavelength variation with a 5 ppm band or simply to ensure that the appropriate mode of the laser is maintained at maximum intensity. This can be used to advantage when using a semi-conductor diode laser in an interferometric apparatus for machine calibration. The present invention makes such devices cheaper practical by easing the requirement for frequency stabilisation such that a variation of up to 5 ppm is allowable.

Alternatively, the invention makes it possible to simplify the pre-processing of the diode laser beam to provide a constant wavelength for a measuring apparatus as will be described later.

Figure 3:
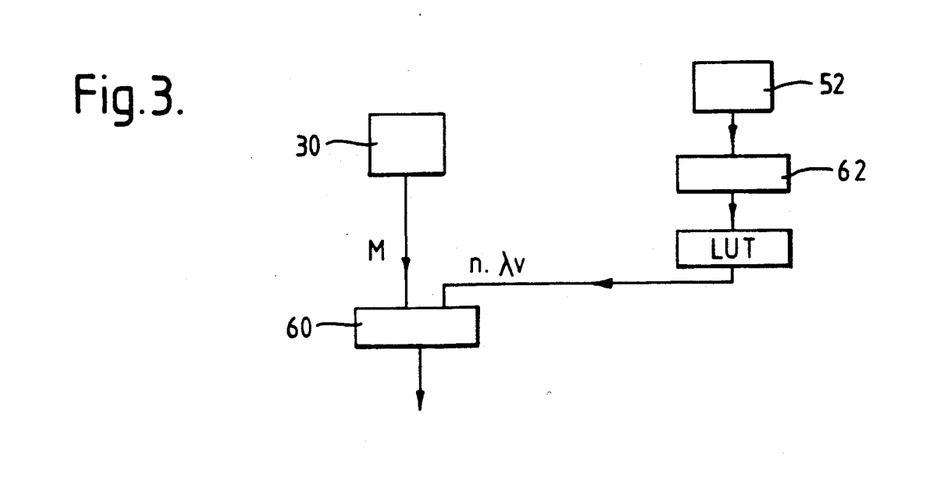
FIG. 3 is a block diagram of the interconnections of post-processing components of the apparatus of FIG. 1.

FIG. 3 illustrates the electronic parts of an interferometric measuring apparatus of the present invention schematically. The fringe count from the detector 30 of the distance measuring interferometer is passed to one side of a multiplying junction 60. The fringe count from the detector 52 of the auxiliary interferometer is passed to an analogue to digital converter 62 and then to a look-up table LUT in which are stored the range of values of $n.\lambda_v$ which have been previously calibrated against the fringe count $\Delta_m$ of the detector 52. The value of $n.\lambda_v$ passed to the other side of the multiplying junction 60, of which the output is a fringe count corrected for wavelength variations.

The cost and relative simplicity of the refractometer and its associated electronics, along with the simplified frequency stabilisation techniques allowed to be used with the interferometric measuring apparatus of the present invention, provide significant savings compared with known systems incorporating absolute refractometers or environmental compensation units. This is particularly true if the auxiliary interferometer is in the form of a simple Mach Zehnder interferometer.

The above description has been based on the assumption that the physical path length difference L remains fixed. Changes in the length L due to temperature can be minimised by making the components from a low expansion material such as that sold under the trade name ZERODUR. Similarly changes due to atmospheric pressure variations and humidity variations should be insignificant so that the assumption should be valid.

The optical components 46,48 should be made as nearly as possible of equal thickness to avoid differential optical path length changes through them due to temperature variations. As long as these differential optical path length changes are kept to an insignificant level however, some tolerance can be allowed on the manufacture of these components.

If it is not convenient to put the auxiliary interferometer close to the measurement interferometer as shown, a temperature difference could exist between the two. Such a temperature difference could be simply determined and allowed for using a thermocouple.

As has been described above the small auxiliary interferometer with its small path difference of 6 mm can act as an absolute air refractometer starting from a known refractive index of air of 1.0002920 by interpolating down to one hundredth of a fringe count to give the nearest 1 ppm change in the refractive index over the chosen of 100 ppm. Thus if the recorded fringe count is +0.25, it shows that the refractive index (ignoring frequency changes or other errors) has changed by 25 ppm to 1.0003170. This interpolation accuracy may be perfectly adequate for many application. Greater accuracy can only be achieved using the above-described design with its 6 mm path difference by increasing the interpolation accuracy and hence the complexity and expense of the interpolator.

It would be possible to increase the accuracy of the auxiliary interferometer by designing a larger instrument with a larger path difference L, but this would be at the risk of reducing the range of refractive index variations over which the interferometer can effectively act as an absolute refractometer, i.e. before it starts to register whole fringe count changes. For example, by choosing a path difference of, say, 600mm, a change of 1 ppm in the refractive index or air would give rise to a whole fringe count change and by interpolating to one hundredth of a fringe count changes in refractive index down to 0.01 ppm could be measured. Such an instrument, however, would have ambiguity in its readings and could not give absolute readings for the refractive index at any time without measuring the initial refractive index first.

However, by providing both a small and a large auxiliary interferometer operating in series off the same laser beam, the ambiguity of the larger interferometer can be removed and the effective absolute measurements can be restored. In such a combination, the small auxiliary interferometer will indicate the integer reading in parts per million of the refractive index while the large auxiliary interferometer will provide the interpolation down to the nearest one hundredth of a part per million.

For example, if as described above, the small auxiliary interferometer shows a reading +0.25, the refractive index is known to have changed from 1.0002920 to 1.0003170. If the larger auxiliary interferometer shows a reading of say, 40.55 fringes, while the change of 40 whole fringes is ambiguous because the initial refractive index is now known, the 0.55 of a fringe shows that in addition to the integer fringe count change there has been a further change of 55 hundredths of a part per million. Hence the absolute refractive index measurement would be 1.00031755.

This combination of two auxiliary interferometers depending on the path differences selected can provide for accurate tracking of refractive index changes with a simultaneous absolute measurement.

Figure 4:
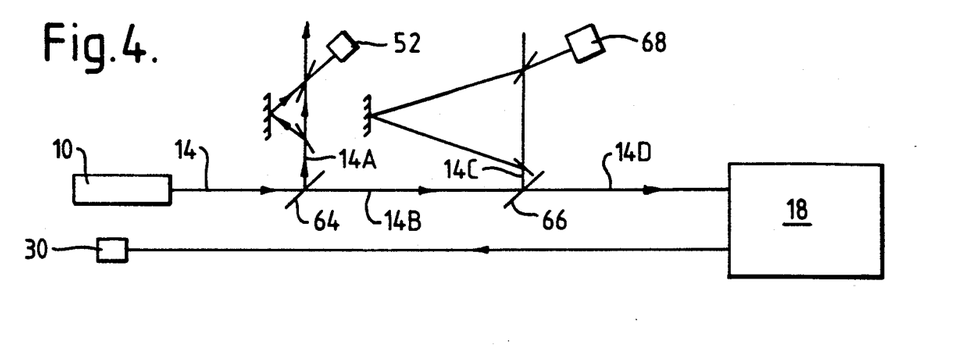
FIG. 4 is a diagrammatic representation of a modification to the interferometric measuring apparatus of FIG. 1.

FIG. 4 illustrates how such a combination may be used. Referring now to FIG. 4 the beam 14 from the laser 10 is split by a first beams splitter 64 which reflects a first part 14A of the beam into the first auxiliary interferometer 40 of the Mach Zehnder type, while transmitting a second part 14B to a second beam splitter 66. The beam splitter 66 reflects a first part 14C of the beam 14B into a second auxiliary interferometer of the Mach Zehnder type, while transmitting a second part 14D to the distance measuring interferometer 18. The first auxiliary interferometer 40 produces a fringe count proportional to the refractive index of the air in its detector 52.

Similarly the second auxiliary interferometer produces a fringe count proportional to the refractive index of air in a detector 68.

Both of the signals from the two auxiliary interferometers are combined to provide a correction signal in the multiplier junction 60.

Figure 5:
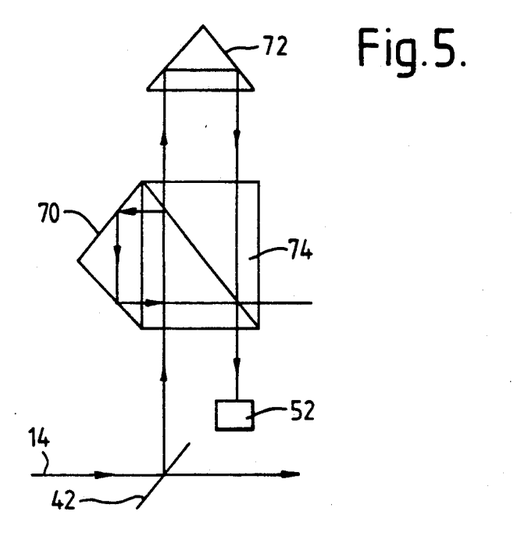
FIG. 5 is an enlarged view of an alternative form of auxiliary interferometer.

Alternatively other forms of auxiliary interferometer may be used, for example, a standard Michelson interferometer as shown in FIG. 5. A beam splitter 42 is provided in the path of the laser beam 14 to provide a deflected beam 44 for the auxiliary interferometer. The path length difference within the Michelson interferometer is established between two retro-reflectors 70 and 72 mounted in fixed relationship from a beam splitter 74 positioned in the path of the light beam 44. One of the retro-reflectors e.g. 70 may be mounted integrally with the beam splitter, and the path difference of 6 mm provided by mounting the other retro-reflector 72 three mm from the beam splitter.

The Mach Zehnder interferometer described above does not fulfil one of the design criteria that the number of surfaces encountered by the light beams in the two beam paths should be the same. This gives rise to possible problems that contamination building up on the surfaces can change the optical characteristics of the surfaces and hence the optical path length. This can be overcome by using materials for the reflecting films which thermally stable optical properties.

Figure 6:
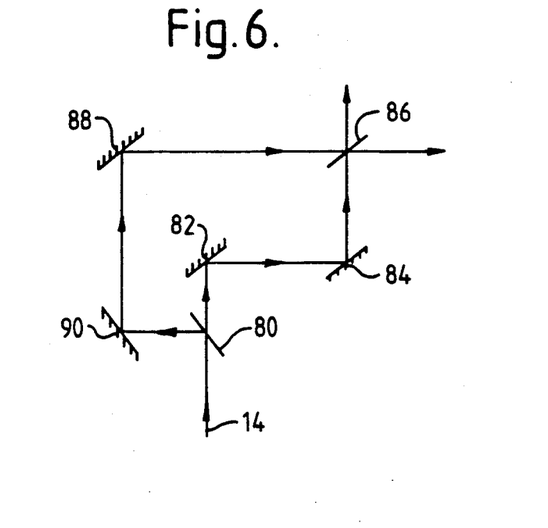
FIG. 6 is an enlarged view of a further alternative form of auxiliary interferometer.

FIG. 6 shows a further alternative arrangement for a refractometer in which uses a beam splitter 80 and a plurality of plane mirrors 82,84,86,88,90 to split a light beam 14 to provide two beam parts which undergo the same number of transmissions and reflections in each part while providing the necessary path difference.

The present invention has been described in combination with a distance measuring interferometer, but it is also possible to use it in combination with other types of interferometer which require a significant path length difference in making measurements, for example an angle measuring interferometer.

It can be seen from the above-described embodiments that the greater the range of the auxiliary interferometer, i.e. the greater the change in refractive index per fringe count generated, the less the ambiguity in the reading, so that the auxiliary interferometer can be made to give absolute readings of the refractive index of the atmosphere. This is achieved however, at the expense of accuracy. For example, the preferred example described in FIG. 2 provided a cheap absolute air refractometer which had a range 100 ppm but an accuracy of only 1 ppm. The larger instrument described in FIG. 4 with a range of 1 ppm had an accuracy of 0.01 ppm but needed an additional absolute air refractometer in combination therewith to determine the initial refractive index of the atmosphere to resolve the ambiguity in its readings. Somewhere between these two extremes it is possible in accordance with the invention disclosed herein to design a low cost system which uses a refractometer having high accuracy but with some ambiguity in its readings (e.g. 10 ppm range and an accuracy of 0.1 ppm). The ambiguity must then be resolved with a crude, low cost, weather station using thermocouples or thermistors to measure temperature, and a barometer to measure pressure, whereby the initial refractive index of the atmosphere can be determined to within 10 ppm to remove the ambiguity from the readings of the auxiliary interferometer.

Figure 7:
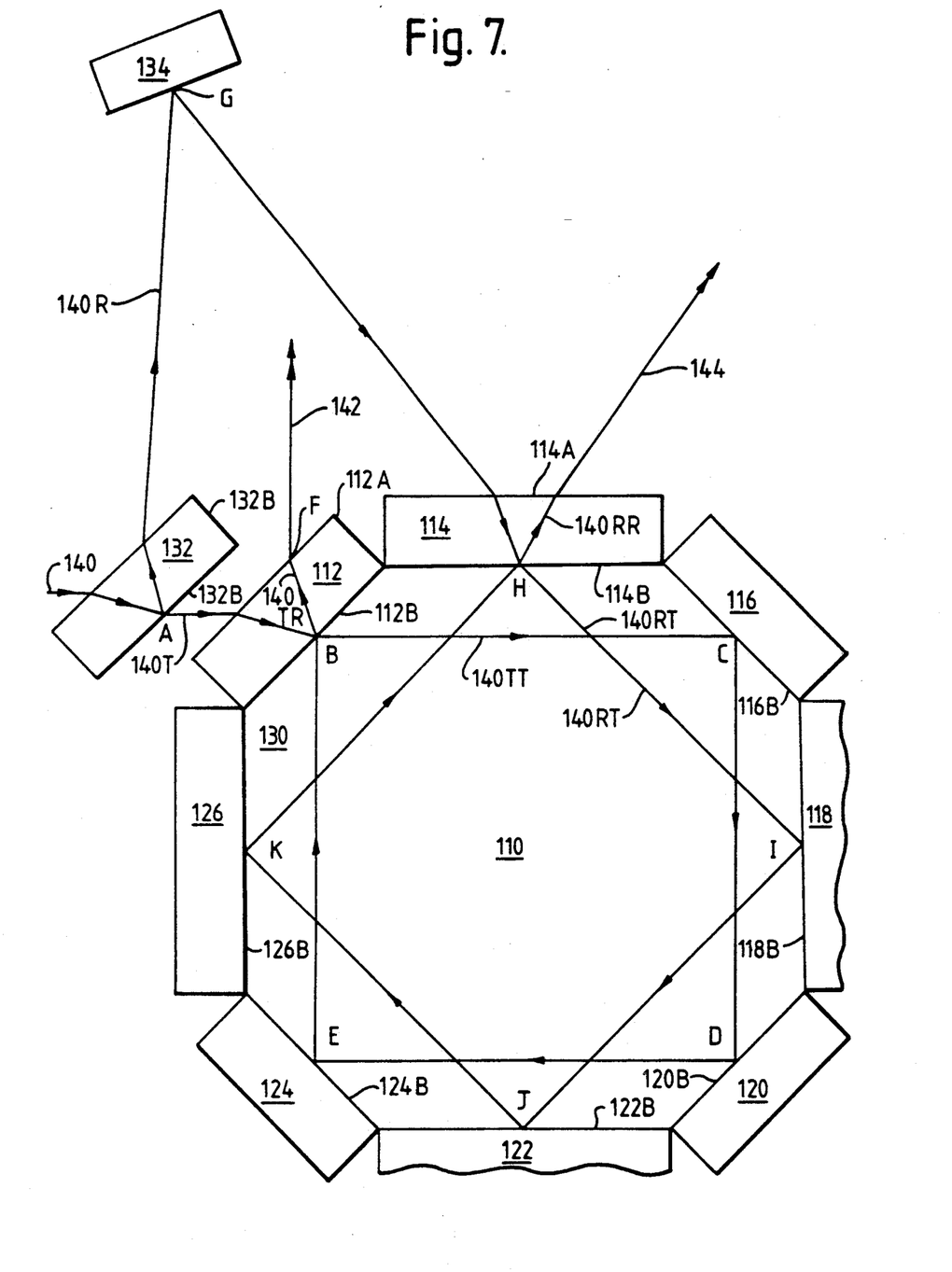
FIG. 7 is a detailed diagram of a further alternative form of auxiliary interferometer which forms a refractometer of the present invention.
Figure 8:
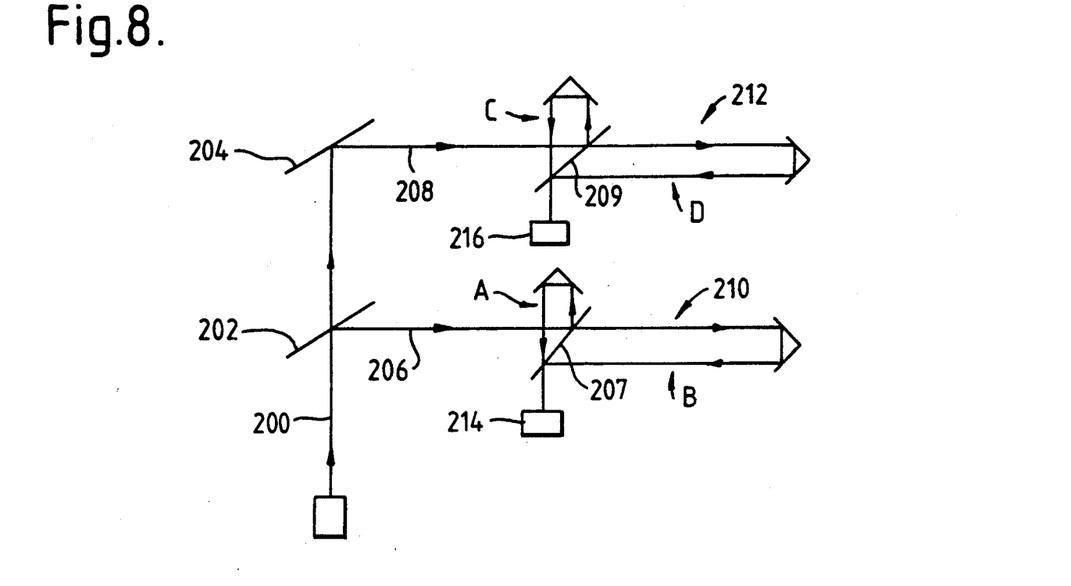
FIG. 8 is a diagrammatic representation of a further alternative design for an auxiliary interferometer using a pair of Michelson interferometers.

A preferred arrangement for improving the accuracy of the refractometer without sacrificing its range is to use a pair of interferometers as shown in FIGS. 7 and 8 below.

Referring now to FIG. 7, there is shown of a refractometer having an octagonal glass base 10 which is, for example, 10 mm thick. Mounted to each of the eight external side faces of the base are parallel-sided glass blocks 112,114,116,118,120,122,124,126 each of which extend upwardly from the base for example by a further 10 mm to provide an open, eight-sided cavity 130.

Two of the glass blocks, 112 and 114 are made as beam splitters, having anti-reflecting coatings on their faces, indicated at 112A and 114A, which are external to the cavity 130, and semi-reflecting coatings on their faces, indicated at 112B and 114B, which are internal to the cavity 130. The remaining glass blocks are provided with reflecting coatings on their faces indicated at 116B,118B,120B,122B,124B and 126B respectively which are internal to the cavity 130.

Mounted in fixed relationship to each other and to the base 110 are a beam splitter 132 and a further reflector 134. Beam splitter 132 has faces 132A and 132B which are respectively coated with an anti-reflecting coating and a semi-reflecting coating.

This arrangement of glass blocks provides two auxiliary interferometers, which produce from an incoming laser beam 140, two emergent beams 142 and 144. The two beams 142,144 with appropriate signal processing, provide information relating to the change in the wavelength of the light constituting laser beam 140, due to variations both in atmospheric conditions and changes in frequency of the laser beam.

In one preferred arrangement of the glass blocks the auxiliary interferometers will not only provide information on a continuous basis relating to variations in atmospheric conditions and laer beam frequency, thus acting as a tracking refractometer, but will also give absolute readings of the refractive index of the atmosphere and thus act as an absolute refractometer over a specified operating range.

The operation of the apparatus is as follows:

The incoming laser beam 140 enters the beam splitter 132 and is split thereby into a transmitted beam 140T and a reflected beam 140R. The transmitted beam 140T passes into the beam splitter 112 and is split thereby at point B into a further transmitted beam 140TT and a further reflected beam 140TR. The transmitted beam 140TT is reflected in a square path around the cavity 130 from points C,D and E on faces 116B,120B and 124B respectively and combines with the reflected beam 140TR at the beam splitter 112 to form the emergent beam 142.

Thus it can be seen that a first interferometer has been formed in which the two parts 140TT and 140TR of the transmitted beam 140T in travelling from a point A on face 132B of beam splitter 132 to point F on the face 112A of beam splitter 112 have followed different paths respectively ABCDEBF and ABF. Since the parts of the beam paths between A and B and between B and F are common the path length difference $L_1$ is simply the distance BCDEB. The path difference $L_1$ will give rise to interference in the combined emergent beam 142 which can be detected in known manner by an interference fringe detection circuit (not shown).

A second interferometer is formed using the reflected part 140R of the beam 140. This beam is reflected at point A to a point G on the reflector 134, at which it is further reflected towards the beam splitter 114. At point H on beam splitter 114, beam 140R is split into a transmitted beam 140RT and a reflected beam 140RR. The transmitted beam 140RT is reflected in a square path around the cavity 130 from points I,J and K on faces 118B,122B and 126B respectively before re-combining at point H with the reflected beam 140RR to form the emergent beam 144.

As in the case of the first interferometer the path length differential is the distance HIJKH within the cavity 130.

Because of the difference $L_2$ in the path lengths there will once again be interference in the combined beam 144 which can be detected by a detection system (not shown).

However, since all of the glass blocks are mounted in fixed relation to each other, the physical path lengths traversed by the various parts of the beam 140, although different, will nominally be fixed. That is, the only variation will be due to thermal expansions or contractions of the base, which can be minimised if the base is made from a low expansion material such as that sold under the trade name ZERODUR.

Thus any interference fringes detected by the detection systems operating on the two combined beams 142 and 144 will be mainly caused due to variations in the optical path lengths of the beam parts due to atmospheric changes.

In the present embodiment the path length differences $L_1$ and $L_2$ of the two interferometers are arranged to be relatively large to give greater accuracy, but the difference between them $L_1$-$L_2$ is arranged to be less than 6 mm in order to maintain the absolute nature of the measurements. In the example shown, path length $L_1$ is 75.8 mm and path length $L_2$ is 70.71 mm giving a difference $L_1$-$L_2$ of 5.09mm.

Taking the Refractive Index of air under standard temperature and pressure conditions $n_1$ as 1.0003, a change in atmospheric conditions such as to increase the refractive index by 100 ppm increase would give a new refractive index $n_2$ of 1.0004. The following calculations are based on these two atmospheric conditions.

Since the physical path lengths $L_1$ and $L_2$ remain unchanged, the optical path lengths in air at the two different atmospheric conditions are given by:

$$L_1' = n_1 \times 75.8 \text{ mm}$$
and
$$L_2' = n_1 \times 70.71 \text{ mm}$$
and
$$L_1'' = n_2 \times 75.8 \text{ mm}$$
and
$$L_2'' = n_2 \times 70.71 \text{ mm}$$
thus
$$L_1'' - L_1' = (n_2 - n_1)\, 75.8 \text{ mm}$$
and
$$L_2'' - L_2' = (n_2 - n_1)\, 70.71 \text{ mm}$$
Since
$$n_2 - n_1 = 1/10^4 \text{ for 100 ppm change}$$
$$L_1'' - L_1 = 7.58 \ \mu m$$
and
$$L_2'' - L_2' = 7.071 \ \mu m$$

With the wavelength $\lambda$ of the light from the $H_e$-$N_e$ laser set at 0.633 $\mu$m the differences in optical path lengths in each case work out to be:

$$7.58/0.633 \approx 11\pi \text{ and } 7.071/0.633 \approx 12\lambda$$

Thus from either one of the interferometers a measurement of the change in refractive index of air can be made with an accuracy down to one tenth of a part per million by interpolating to $100^{th}$ of a fringe count.

However, if the change in refractive index from that at standard conditions is greater than ten parts per million the fringe count will have moved by more than one and uncertainty is introduced into the measurement. This uncertainty can be resolved by taking the difference in the readings of the two interferometers which as explained above effectively gives an indication of the fringe count change over a path difference of 5.09mm, and thus an indication of the absolute value of the change in the refractive index.

The absolute value of the change in refractive index can then be obtained in either of two ways.

Firstly, as described above, the first interferometer (which measures $L_1$) has been designed to have a path length increase of 12 wavelengths ($\lambda$) for a 100 ppm increase in refractive index, and the second interferometer has been designed to have a path length increase of 11 wavelengths for the same increase in refractive index. Thus while the refractive index increases from 1 to 100 ppm the fringe counts of the two interferometers are increasing in the range 0 to $12\lambda$ and 0 to $11\lambda$ respectively, and the difference in the two interferometer fringe counts is increasing gradually from 0 to 1 in a progression related to the ratio 12:11. This difference thus enables the absolute change in refractive index to be uniquely determined within the 100 ppm range.

For example, when the system is switched on the two fringe counters will each indicate a path length change ($\Delta L_1$ or $\Delta L_2$), of only a fraction of a fringe count as determined by the interpolators, since the counters have had no integer fringe counts to count (or they will show a meaningless integer fringe count plus the fraction). Since the two fractions are related by the ratio of the wavelength ranges, the difference between the two fractions will uniquely identify which part of the range of the fringe count of either interferometer the fraction lies in, and thus provide the missing integer fringe count. This can be used to give an absolute value for the change in refractive index from a calibration table.

Alternatively, because each interferometer respectively records a fringe count in the range 0 to $11\lambda$ or 0 to $12\lambda$ for the same change in the refractive index in the range 0 to 100 ppm, so that the two readings will be related by the ratio 11:12, it follows that within these ranges the difference between the readings will be a different but unique value for any two readings. Since the difference between the readings is always less than 1 fringe count, it means that the two fractions of a fringe count provided by the interpolators of the two interferometers detection systems will only occur together at one point within the range, thus uniquely identifying that part of the range in which the fringe counts lie.

Hence a pre-programmed look-up table can be provided in the detector system the inputs to the two areas of which are all of the possible readings of the first detector from 0 to $12\lambda$ against all of the corresponding readings of the other interferometer from 0 to $11\lambda$ in steps of hundredths of a fringe count. Then in the table are provided the values from either one of the interferometer readings of the integer wavelengths at which the two readings occur simultaneously.

To avoid having to use a further calibration table, the value in ppm of the change in refractive index calibrated from the detector readings of one of the interferometers may be put into the table in place of the wavelength data.

The invention therefore provides two interferometers using a single common cavity defined by a geometric shape which enables the components which define it to also be of simple shape and thus relatively easy to manufacture. Clearly shapes other than an octagon may be used for the base without losing the benefit of the invention.

However, having an octagonal shape providing two interferometers, the light paths through each of which define a square, gives good symmetry of the light paths and enables simple rectangular glass blocks to be used for forming the mirrors and beam splitters. It can also be seen that within the cavity 130 the beams do not pass through any glass, and both beams 140TT and 140RT undergo the same number of reflections. Problems of differential temperature variations and surface contamination are thus minimised.

Because the interferometer cavity is square the reflecting coatings on the faces 112B,114B,116B,118B,120B,122B,124B and 126B are not fully reflecting so that the intensity of the light beams 140TT and 140RT is significantly reduced as they are reflected around the square. This reduces the problems of interference in the light beams in the square. As an example, the coatings on the faces 112B and 114B of the beam splitters may be 10% reflecting and 90% transmitting. Then the coefficients of the reflecting coatings on the remaining glass blocks are calculated to ensure that the intensities of the transmitted and reflected portions of the combined beams 142 and 144 are substantially equal.

As a further aid to reducing interference within the beams in the cavity 130, the beam splitter 114A may be angled very slightly (for example at 0.2°) so that the reflected beam portion 140RR and the transmitted beam portion 140RT of the combined beam 144 do not align exactly and a spatial spread of the interference fringes produced in the combined beam is achieved. This also ensures that within the cavity the part of the beam 140RT which is reflected from face 114B of the beam splitter 114 after one passage around the square block will be mis-aligned with beam 140RT the second time around and will have less tendency to interfere.

The beam splitter 112 may also be fitted slightly out of alignment to achieve the same objects of spatially spreading the interference pattern of the combined beam 142 and avoiding interference in the transmitted beam 140TT within the interferometer cavity 130.

The two interferometers described above may be used in operation as auxiliary interferometers in an interferometric measuring apparatus for correcting errors in the measurements made by the apparatus due to change in the refractive index of the atmosphere during the measuring process. For this purpose, the laser beam used in the auxiliary interferometers is preferably derived from the laser beam used in the measuring apparatus by a beam splitter, and the octagonal cavity 130 defined by the various glass blocks is open to the same atmosphere as the measuring apparatus.

A further embodiment of the invention in which the refractometer is formed from a pair of Michelson interferometers is shown in FIG. 8. In this embodiment a laser beam 200 is split twice by beam splitters 202,204 into two beams 206,208 directed at two interferometers 210,212. Each interferometer has a beam splitter 207,209 producing two fixed internal path lengths A and B, C and D respectively, and detectors 214,216 respectively provide fringe counts if variations in the refractive index of the atmosphere cause the optical path lengths to change.

By keeping the individual path differentials A−B and C−D relatively long, but the difference between the path differences L=(A−B)−(C−D) close to 6 mm as above, high accuracy can also be obtained from this embodiment as a tracking interferometer while maintaining the capability of measuring absolute values of the refractive index of the atmosphere.

Although the above embodiments have been described for use in correcting the measurements of a measuring interferometer for changes in refractive index, the signals from the detectors of refractometers of the present invention may be used for other purposes.

Figure 9:
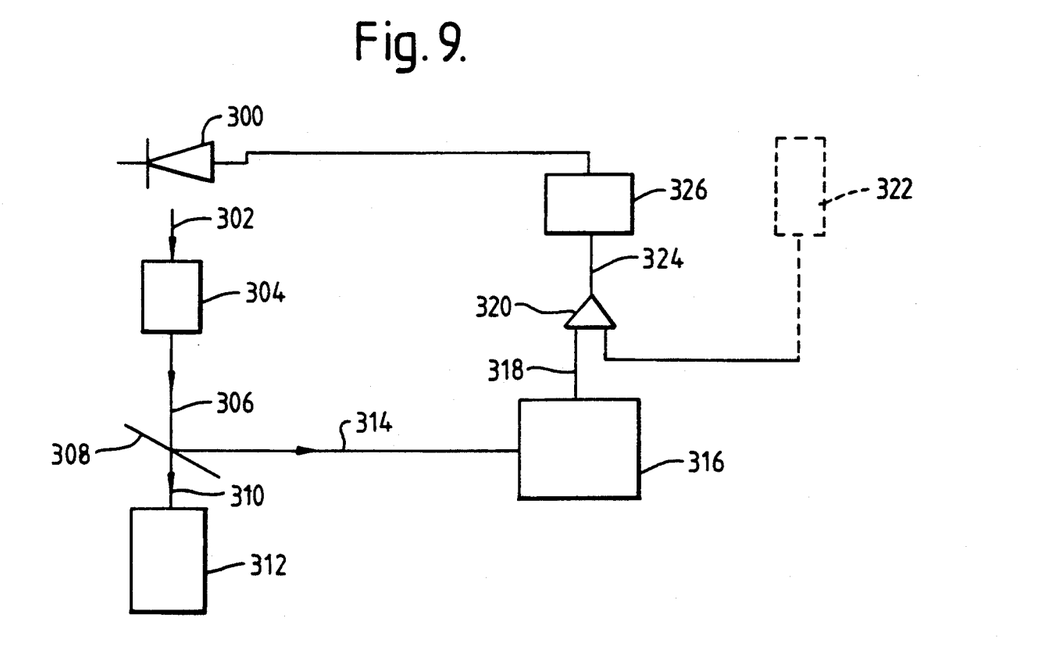
FIG. 9 is a schematic representation of a control system for using the auxiliary interferometer information to control a parameter of a diode laser.

FIG. 9 shows a method of using the signal from the air refractometer to vary the frequency of the laser light source in response to changes in refractive index so that the wavelength of the light passing through the measuring interferometer and the refractometer remains constant. By virtue of this pre-processing of the laser, there is no need to perform any corrections on the measurements made by the measuring interferometer.

This has particular advantages when a diode laser is used as the light source since such a laser has a relatively large tunable frequency range.

The overall system includes a laser diode 300 for producing a coherent light beam 302 which is directed through a collimator 304 to produce a collimated light beam 306 directed toward a beam splitter 308. The beam splitter produces a transmitted beam 310, which is to be used for the measuring interferometer 312, and a reflected beam 314 which is passed to an air refractometer 316, which may be of any of the forms encompassed by the present invention.

The signal 318 from the air refractometer is delivered as a fringe count to a comparator 320, to which is also delivered a fixed value for comparison. This fixed value may be generated by a computer 322 which includes the look-up table and performs the calculations required to obtain the desired measurements.

If a change occurs in the refractive index of air the comparator generates an error signal 324 which is passed to a control unit 326. The control unit controls the current being supplied to the laser diode which in turn varies the frequency of the laser beam produced by the laser diode such as to keep the wavelength of the laser beam through the refractometer, and hence through the measuring interferometer at a constant value.

This avoids the need for correcting the measurements made by the measuring interferometer. The use of the refractometer of the present invention which gives absolute measurements of the refractive index enables the wavelength of the laser diode to be adjusted to, and maintained at a specific value so that measurements to a traceable standard can be made with the measuring interferometer.

The wavelength control system for the laser diode which derives its control signal from an air refractometer of the present invention can provide long term wavelength stability if used in conjunction with a dual interferometer form of refractometer. These forms of refractometer by virtue of their common mode characteristics, i.e. each beam path length having the same number of reflections and passing through the same length of glass, does not suffer from drift in its measurements of refractive index.

The auxiliary interferometer system of FIG. 7 shows glass blocks producing a four-sided arrangement for the two interferometers. This is a preferred arrangement which produces a fringe spacing in the detector which is independent of the angle of incidence of the incoming laser beam. Other arrangements of glass blocks producing multiple sides figures having different numbers of sides may however be used.

We claim:
1. A gas refractometer comprising:
a light source for providing a light beam of known nominal frequency;
an interferometer system including at least one interferometer, said system having beam splitting means for splitting said light beam into a plurality of beam parts, and for combining said split beam parts into at least one outgoing beam from the interferometer system; and a detector system for receiving said at least one outgoing beam, and for deriving from said at least one outgoing beam an output in the form of a fringe count corresponding to a change in wavelength of said beam parts in the interferometer system, wherein the interferometer system includes means for defining beam paths of unequal physical path lengths, the difference in said physical beam path lengths being fixed, so that, depending on said nominal frequency of said light beam, the maximum change in wavelength of said beam parts due to variations in at least one of said nominal frequency and a refractive index of the atmosphere will change the detector system output by less than one fringe count.

2. A gas refractometer according to claim 1, wherein said interferometer system comprises a single interferometer and said beam splitting means comprises: a first beam splitter for producing a transmitted beam part and a reflected beam part; and a second beam splitter for combining said two beam parts to form an outgoing beam from said interferometer system, the output of the detector system being a fringe count generated from said outgoing beam and corresponding to a change in wavelength of said transmitted beam part and said reflected beam part.

3. A gas refractometer according to claim 1, wherein said interferometer system comprises two interferometers which produce two outgoing beams and the output of said detector system is derived by taking the difference in fringe counts generated by the two outgoing beams.

4. A gas refractometer according to claim 1, wherein said interferometer system comprises two interferometers having a common cavity and said beam splitting means comprises two beam splitters each producing transmitted and reflected beam parts for each of said interferometers, wherein said transmitted beam parts, one from each beam splitter, each traverse different physical path lengths through said common cavity before being combined with said reflected beam parts to produce two outgoing beams from said interferometer system, the output of said detector system being a fringe count derived from the fringe counts generated by said two outgoing beams and corresponding to a change in wavelength of said two of said transmitted beam parts which traverse the common cavity of said two interferometers.

5. A gas refractometer as claim in claim 1, wherein said light source is a Helium-Neon laser and the difference in the physical beam path lengths of said two beam parts is less than 6 mm.

6. A gas refractometer as claimed in claim 1, wherein said light source is a semi-conductor diode laser.

7. A gas refractometer as claimed in claim 1, wherein the optical path lengths of said beam parts passing through said interferometr system include the same lengths of solid medium.

8. A gas refractometer as claimed in claim 1, wherein said beam parts passing though said interferometer system meet the same number of reflecting surfaces.

9. A gas interferometer according to claim 1 in combination with an interferometric measuring system, said interferometric measuring system comprising an interferometer arranged to receive a portion of light from said light source, and a detector for producing from said portion of said light a measurement output signal, wherein means are provided for applying said output signal from said detector system of said refractometer as a correction signal to correct the measurement output signal of said interferometer for any changes in wavelength of said light passing through said interferometer.

10. A gas refractometer in combination with an interferometric measuring system according to claim 9, wherein the frequency of said light source is maintained at a known nominal value whereby said output signal from said detector system of said refractometer corrects said measurement output signal of said interferometer for variations in wavelength of said light passing through said interferometer caused by changes in said refractive index of the atmosphere in which said interferometric measuring system is used.

11. A gas refractometer in combination with an interferometric measuring system according to claim 9, wherein said output signal from said detector system of said refractometer corrects said measurement output signal of said interferometer for variations in wavelength of said light passing through said interferometer caused both of variations in the frequency of said light source and by changes in said refractive index of the atmosphere in which said interferometric measuring system is used.

12. A gas refractometer according to claim 6, wherein said output from said detector system is applied as a correction signal to said laser diode to maintain the wavelength of said light beam from the laser diode constant.

13. A gas refractometer according to claim 12 in combination with an interferometric measuring system, said interferometric measuring system comprising an interferometer arranged to receive a portion of said light from said laser diode, and said detector system produces from said portion of said light a measurement output signal.

14. A gas refractometer comprising:
a light source for generating a light beam of known nominal frequency,
an interferometer, including beam splitting means, for producing from said light beam two beam parts and for combining said beam parts to produce an outgoing light beam from said interferometer, and further including means for defining beam paths for said beam parts through said interferometer which are of unequal physical lengths,
a detector system for receiving said outgoing light beam and for producing therefrom an output signal in the form of an interference fringe count indicative of a change in wavelength of said beam parts within said interferometer,
wherein the difference between said physical path lengths of said beam parts is fixed and is arranged, depending on the nominal frequency of light from said light source, to be such that the maximum change in wavelength of said beam parts due to variations in at least one of the frequency of light from said source and a refractive index of the atmosphere will result in a change in said interference fringe count in said detector system of less than one.

15. A gas refractometer comprising:
a light source for generating a light beam of known nominal frequency, an interferometer system including two interferometers, said system having beam slitting means for producing from said light beam respective beam parts for each of said interferometers and for combining said beam parts into two outgoing beams from said interferometer system, a detector system for receiving said two outgoing beams, and for deriving therefrom an output in the form of a fringe count corresponding to a change in wavelength of said beam parts in said two interferometers, wherein said interferometer system includes means for defining beam paths of unequal physical path lengths for said beam parts within said interferometers, the differences in said physical beam path lengths being fixed and being such that depending on said nominal frequency of said light beam, the maximum change in wavelength of said two beam parts due to variations in at least one of said nominal frequency and the refractive index of the atmosphere will change said output of said detector system by less than one fringe count.

16. A gas refractometer according to claim 15, wherein said two interferometers have a common cavity and the beam splitting means comprises two beam splitters each producing transmitted and reflected beam parts for each of said interferometers, two of said beam parts, one from each beam splitter, traversing different physical path lengths through said common cavity before being combined with the other beam parts to produce said two outgoing beams, the output of said detector system being a fringe count derived from the fringe counts generated by said two outgoing beams and corresponding to a change in wavelength of two of said beam parts which traverse said common cavity of said two interferometers.

17. A gas refractometer according to claim 16, wherein said common cavity is defined by a plurality of reflecting surfaces, said transmitted beam parts from each of said beam splitters being reflected around said cavity by said reflecting surfaces to be combined with said reflected beam parts to form said two outgoing beams.

18. A gas refractometer according to claim 17, wherein said common cavity is defined by an octagonal arrangement of glass blocks, two of which form said two beam splitters.

* * * * *